United States Patent [19]

Irikura et al.

[11] Patent Number: 4,593,092
[45] Date of Patent: Jun. 3, 1986

[54] CLASS OF SPIRO-LINKED PYRROLIDINE-2,5-DIONES

[75] Inventors: Tsutomu Irikura, Tokyo; Koichi Takagi, Omiya; Shizuyoshi Fujimori, Nogi; Yoshihiro Hirata, Omiya, all of Japan

[73] Assignee: Kyorin Pharmaceutical Co., Ltd., Tokyo, Japan

[21] Appl. No.: 685,804

[22] Filed: Dec. 24, 1984

[30] Foreign Application Priority Data

Dec. 28, 1983 [JP] Japan ................................ 58-246799

[51] Int. Cl.$^4$ .................. C07D 498/20; C07D 513/20; C07D 487/20
[52] U.S. Cl. ......................................... 544/6; 544/70; 546/15
[58] Field of Search ........................ 544/6, 70; 546/15

[56] References Cited

U.S. PATENT DOCUMENTS 4,478,847 10/1984 Brittain et al. ............... 548/410 X
4,503,066  3/1985 Brittain et al. ............... 548/410 X

OTHER PUBLICATIONS

Sarges, Chemical Abstracts, vol. 91 (1979) 20510y.
Sarges, Chemical Abstracts, vol. 92 (1980) 94401f.

Primary Examiner—Richard L. Raymond
Attorney, Agent, or Firm—Oblon, Fisher, Spivak, McClelland & Maier

[57] ABSTRACT

The invention provides a novel spiro-linked pyrrolidine-2,5-dione of the formula;

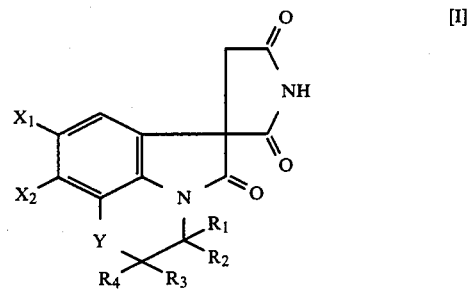

wherein $X_1$ and $X_2$ each independently represent a hydrogen, a halogen atom, a lower alkyl or lower alkoxy group; Y is a methylene group, oxygen or sulfur atom; $R_1$, $R_2$, $R_3$ and $R_4$ each independently represent a hydrogen atom, a lower alkyl group or forming a benzene ring together with their adjacent carbon atoms; the base salts thereof with pharmaceutically acceptable cations, and processes for their manufactures.

The compounds of formula [I] useful as aldose reductase inhibitors and as therapeutic agents for treatment of chronic diabetic complications are also disclosed.

8 Claims, 1 Drawing Figure

CLASS OF SPIRO-LINKED PYRROLIDINE-2,5-DIONES

BACKGROUND OF THE INVENTION

This invention relates to new spiro-linked cyclic imido derivatives having the property of inhibiting the enzyme aldose reductase in vivo, their base addition salts and processes for their manufacture.

In the present market of pharmaceuticals, such antidiabetic agents as sulfonyl ureas are only used for symptomatic treatment against hyperglycemia, but little effective for reduction of prevention of diabetic complications.

It has been shown that aldose reductase was involved in diabetic complications such as diabetic cataracts, neuropathy and retinopathy (J. H. Kinoshita et al., JAMA, 246, 257, −81). Enzyme aldose reductase catalyzes the reduction of aldoses such as glucose and galactose to form polyols such as sorbitol and galactitol. These polyols penetrate cell membranes poorly and, once formed, tend to be removed only by further metabolism so that net effect is an accumulation of them inside the cell. In such hyperglycemia as diabetes mellitus, the higher sugar level activates aldose reductase to accelerate the further conversion of glucose to sorbitol. As a consequence, sorbitol accumulates abnormally within the cell, for example in the lens, peripheral nerve, kindney and vascular tissues, causing a rise in internal osmotic pressure and creating a hypertonic condition which may be in turn sufficient to destroy or impair the function of the cell themselves. Therefore, it may be of therapeutic value for controlling certain chronic diabetic complications by depressing of polyols responsible for systematic dysfunctions. That is to say, function in system may be able to maintain normally by inhibiting aldose reductase activity and followed by preventing the abnormal accumulation of olyols.

SUMMARY OF THE INVENTION

This invention relates to new spiro-linked cyclic imido derivatives having the property of inhibiting the enzyme aldose reductase in vivo, their base addition salts and processes for their manufactures.

More particularly, the compounds of this invention are spiro-linked pyrrolidine-2,5-dione derivatives represented by the general formula;

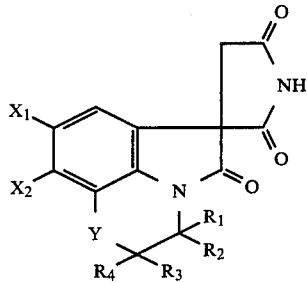

[I]

Wherein $X_1$ and $X_2$ are each independently represent a hydrogen, halogen, a lower alkyl or lower alkoxy group; Y is a methylene group, oxygen or sulfur atom; $R_1$, $R_2$, $R_3$ and ech independently represent a hydrogen, a lower alkyl group or forming a benzene ring together with their adjacent carbon atoms.

More specifically in the compounds of formula [I], the term "lower alkyl" as used in $X_1$, $X_2$, $R_1$, $R_2$, $R_3$ and $R_4$ means straight or branched hydrocarbons having 1 to 3 carbon atoms, such as methyl, ethyl, n-propyl or isopropyl. The term "lower alkoxy" as used in $X_1$ and $X_2$ means alkoxy groups having 1 to 3 carbon atoms, such as methoxy, ethoxy, n-propoxy or isopropyloxy. The term "halogen atom" as used in $X_1$ and $X_2$ means fluorine, chlorine, bromine or iodine atom. Y means a methylene group, oxygen or sulfur atom. When $R_1$, $R_2$, $R_3$ form a ring together with their adjacent carbon atoms, the ring means a benzene.

The compounds of formula [I] are the derivatives of 5',6'-dihydrospiro[pyrrolidine-3,1'-[4H]pyrrolo[3,2,1-ij]quinoline]-2,2',5(1'H)-trione, 2',3'-dihydrospiro[pyrrolidine-3,6'-pyrrolo[1,2,3-de][1,4benzoxazine]-2,5,5'(6'H)-trione, 2',3'-dihydrospiro[pyrrolidine-3,6'-pyrrolo[1,2,3-de][1,4]benzothiazine]-2,5,5'(6'H)-trione and spiro[pyrrolidine-3,2'-pyrrolo[3,2,1-kl]phenothiazine]-1',2,5(2'H)-trione which will be numbered throughout this specification as follows;

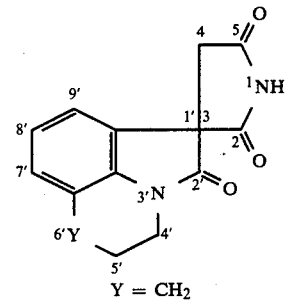

Y = CH$_2$

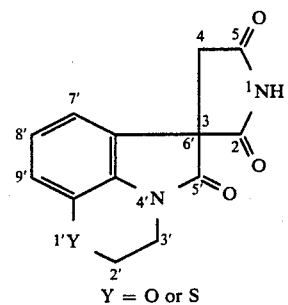

Y = O or S

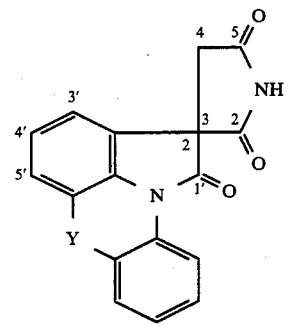

Particular salts of compounds of formula [I] with metals affording a pharmaceutically acceptable cation are, for example, alkali metal or alkaline earth metal salts, such as sodium, potassium, calcium or magnesium salts, and also copper and zinc salts.

The compounds of formula [I] all possess one to two asymmetric carbon atoms, namely at least the spiro carbon atom at position 3 of the pyrrolidine ring. The compounds of formula [I] therefore exist in one or more racemic and optically-active forms. It is naturally to say that this invention encompasses the compounds of formula [I] in racemic form or in any optically-active form.

The novel spiro-linked pyrrolidine-2,5-diones provided by this invention are useful in the reduction or prevention of the development of certain chronic complications arising from diabetes mellitus, such as cataracts, neuropathy, nephropathy and retinopathy.

DETAILED DESCRIPTION OF THE INVENTION

For the purpose of providing the useful agent for treatment of certain complications arising from diabetes mellitus, a series of aldose reductase inhibitors have been widely studied.

However, these studes have not been succeeded yet.

As a result of our continuous and zealous studies for a development of an useful agent for these diseases, we have now completed this invention through the discovering that certain spiro-linked pyrrolidine-2,5-diones of formula [I] possess a potent aldose reductase inhibitory activity in vitro and also in vivo.

The novel compounds of this invention may be obtained by any process known in the art for the manufacture of structurally analogous compounds. Such process are illustrated by the following procedures in which, unless otherwise stated, $X_1$, $X_2$, Y, $R_1$, $R_2$, $R_3$, and $R_4$ have any of the above mentioned meanings.

To an unsaturated compound of the formula;

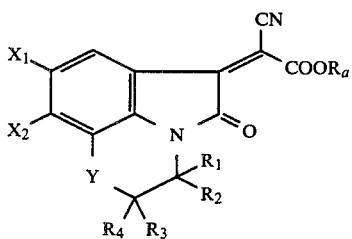

[V]

wherein $R_a$ is a lower alkyl group, or a geometric isomer or an optical isomer thereof, is added cyanide, for example by reacting a compound of the formula [V] with potassium cyanide in methanol at a temperature in the general range 10° to 50° C., to afford a bifunctional derivative of the formula;

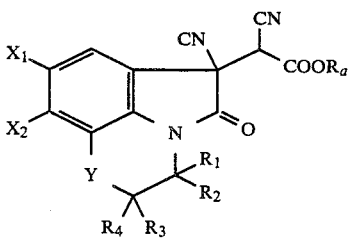

[VI]

wherein $R_a$ is a lower alkyl group.

The compound of formula [VI] is not usually isolated and is permitted to cyclize in situ. That is, the cyclization is performed in the presence of an inorganic acid catalyst such as hydrogen halide, sulfuric acid or polyphosphoric acid in a suitable solvent, for example an alkanol such as methanol, by heating at a temperature range of 20° to 120° C. There is thus obtained a carboxylic acid ester of the formula;

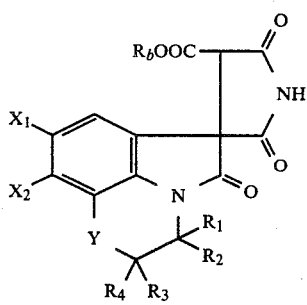

[VII]

wherein $R_b$ is a hydrogen atom and a lower alkyl group. Subsequently, decarboxylation of an acid of the formula [VII] wherein $R_b$ is a hydrogen atom, affords the compound of formula [I by heating. The decarboxylation may be carried out at a temperature in the range, for example 60° to 250° C., and a suitable solvent or diluent, for example acetic acid, diethylamine or quinoline.

An acid of the formula [VII], wherein $R_b$ is a hydrogen atom, is conveniently obtained in situ by hydrolysis of an acid ester of the formula [VII], wherein $R_b$ is a lower alkyl group, using conventional acid or base catalyzed conditions at a temperature range of 40° to 100° C. When base catalysis is used, the acid must be generated from the salt first obtained by acidification with a mineral acid. When acid catalysis is used, it is conveniently able to undergo the hydrolysis followed by spontaneous decarboxylation.

Decarboxylation is able to perform without isolation or purification of an acid ester of the formula [VII] defined above. That is to say, particularly convenient conditions for the in situ formation and subsequent decarboxylation of an acid of the formula [VII] defined above are provided by heating an acid ester of the formula [VII] defined above in alkanoic acid such as acetic acid or propionic acid, in the presence of an inorganic acid such as hydrochloric acid or hydrobromic acid, and at a temperature range of 100° to 120° C.

By the way mentioned above, there is obtained a spiro-linked pyrrolidine-2,5-dione of the formula;

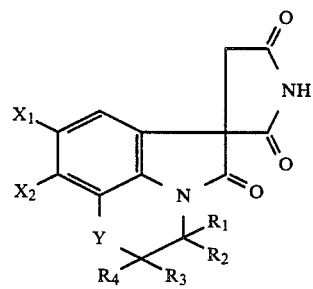

[I]

The compounds of formula [I] thus obtained can be isolated and purified by conventional methods, for example solvent extraction, crystallization or chromatography and so on.

The starting materials of formula [V] are obtained from the corresponding 1,7-cyclic indoline-2,3-diones of the formula;

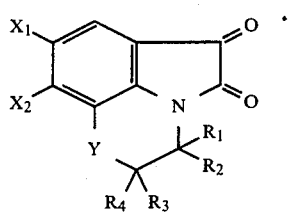

[VIII]

by condensation with ethyl cyanoacetate or methyl cyanoacetate, preferably in the presence of a base catalyst such as piperidine or morphine, in a suitable solubent such as lower alkanol, and at a temperature range of 10° to 100° C.

A few compound of the formula [VIII] has been known in the art. For example, the compound of formula [VIII] wherein Y is a methylene group and $X_1$, $X_2$, $R_1$, $R_2$, $R_3$ and $R_4$ are hydrogen atoms, and the compound of formula [VIII] wherein Y is sulfur, $R_1$, $R_2$, $R_3$ and $R_4$ form a benzene ring together with their adjacent carbon atoms and $X_1$ and $X_2$ are hydrogen atoms, have been obtained from 1,2,3,4-tetrahydroquinoline and phenothiazine by reaction with oxalyl chloride and cyclization by sulfuric acid or aluminum chloride, respectively.

On the other hand, we found a convenient method preparing the compound of formula [VIII] in high yield under mild conditions. Such processes are illustrated by the following procedures representing by general formulas in which Y, $X_1$, $X_2$, $R_1$, $R_2$, $R_3$ and $R_4$ have any of the above mentioned meanings and are included on a further feature of this invention.

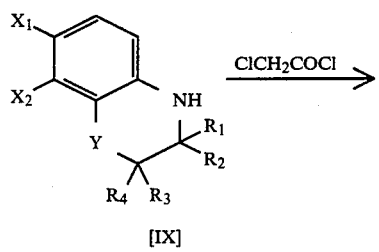

[IX]

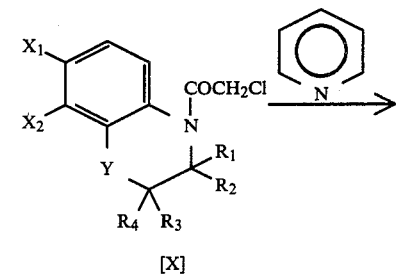

[X]

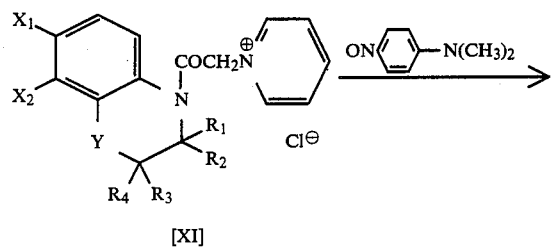

[XI]

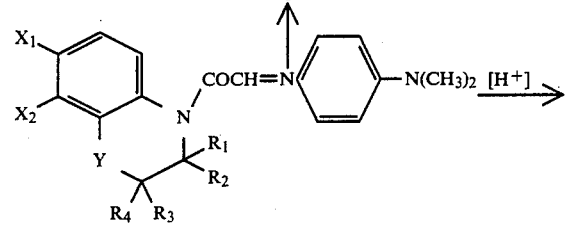

[XII]

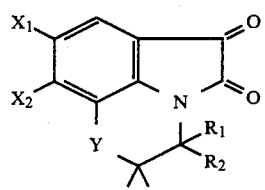

[XIII]

A cyclic amine displayed by formula [IX] (for example, 1,2,3,4-tetrahydroquinoline, phenothiazine, 3,4-dihydro-2h-1,4-benzoxazine, 2,4-dihydro-2H-1,4-benzothiazine or substituted derivatives thereof) is treated with a compound such as monohalogeno acetyl chloride to afford a monohalogeno acetyl derivative [X], which forms a pyridinium halide [XI] in pyridine. A pyridinium salt of formula [XI] readily reacts with an appropriate aromatic nitroso compound such as p-nitrosoaniline or preferable p-nitroso-N,N-dimethylaniline in the presence of a base to afford a nitrone [XII] and such process is known as Krönke reaction. This nitrone [XII] can be cyclized to give a compound of formula [VIII] in high yield by treatment with an inorganic acid such as hydrochloric acid, diluted sulfuric acid or polyphosphoric acid.

These preparing processes of the compounds of formula [VIII] are particularly suitable for the production of them having several substituents and for large scale manufacture since a series of reaction is performed under milder conditions in comparison with severe conventional processes employing the heating with strong acids, and in high yield.

Certain compounds of formula [I] can be prepared not only by above mentioned procedures but also by introducing the substituents by reaction with the corresponding unsubstituted compounds. More specifically, a compound of the formula [I] wherein $X_1$ is a chlorine or bromine atom, is obtained by chlorination or bromination of a compound of the formula [I] wherein $X_1$ is a hydrogen atom. The chlorination or bromination may be carried out using conventional procedures, for example using elemental chlorine or bromine, optionally in the presence of such a catalyst as ferric chloride or ferric bromide at a temperature range of 10° to 100° C., and in a suitable solvent or diluent, for example chloroform, carbon tetrachloride or acetic acid.

Alternatively, the chlorination or bromination may be carried out using sulfuryl chloride or sulfuryl bromide, if necessary in the presence of iodine as catalyst at a temperature range of 10° to 100° C., and in a suitable solvent or diluent, for example acetic acid or chloroform.

Whereafter, when a pharmaceutically acceptable salt is required, compounds of the formula [I] in free base forms is reacted with a base affording pharmaceutically acceptable cation using conventional procedures well known in the art.

Further, when an optically-active form of compound of formula [I] is required, a racemic form of the said compound may be reacted with optically-active form of a suitable organic base, for example brucine, coniine, 2-pipecoline or N,N,N-trimethyl-(1-phenylethyl)ammonium hydroxide followed by conventional separation of the diastreoisomeric mixture of salts or complexes thus obtained, for example by fractional crystallization from a suitable solvent, for example $C_1$ to $C_4$-alkanol, whereafter an optically-active form of the said compound may be liberated by treatment with an aqueous mineral acid such as diluted hydrochloric acid.

The compounds of this invention obtained above have a potent inhibitory activity on aldose reductase as shown by following experiments and are useful for reduction or prevention of the development of chronic complications arising from diabetes mellitus. The compounds of this invention may be administered to subjects in need of treatment for complications by a variety of conventional routes of administration by use of oral or parenteral compositions (for example, an appropriate opthalmic solution) thereof.

EXPERIMENT 1

Figure 1:
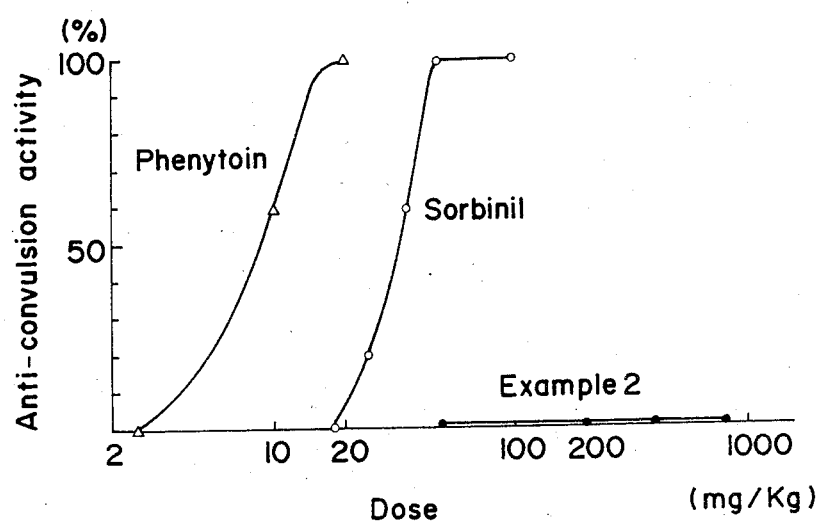
FIG. 1 is a diagram showing a relation between dose of the compound of Example 2 by this invention, Sorbinil and Phenytoin of the comparative compounds, and anti-convulsion activity thereof, respectively.

[Inhibitory activity on aldose reductase in vitro]

The inhibitory activities of compounds on aldose reductase activity were tested according to the procedure of Hayman et al. (J. Biol. Chem., 240, 877, '65). Aldose reductase preparation used in this test was partially purified enzyme from rat lens.

Data are shown in Table 1. $IC_{50}$ values are the molar concentrations required for 50% inhibition against the activity of aldose reductase.

TABLE 1

| Compound of | $IC_{50}$ (M) |
| --- | --- |
| Example 1 | $6 \times 10^{-6}$ |
| Example 2 | $4 \times 10^{-7}$ |
| Example 3 | $9 \times 10^{-6}$ |
| Example 4 | $3.5 \times 10^{-7}$ |
| Example 5 | $5 \times 10^{-6}$ |
| Example 6 | $3.5 \times 10^{-7}$ |
| Example 7 | $2 \times 10^{-6}$ |
| Example 8 | $6 \times 10^{-7}$ |
| Example 11 | $2 \times 10^{-6}$ |
| Example 12 | $1.5 \times 10^{-6}$ |
| Example 13 | $2 \times 10^{-7}$ |
| Example 14 | $7 \times 10^{-7}$ |
| Example 15 | $7 \times 10^{-7}$ |
| Example 16 | $2.5 \times 10^{-6}$ |
| Example 17 | $3.5 \times 10^{-5}$ |
| Standard drug* | $5 \times 10^{-7}$ |

*note; Sorbinil [(4S)-2,3-dihydro-6-fluorospiro[4H—1-benzopyran-4,4'-imidazolidine]-2',5'-dione]

These results show that the present compounds have a potent inhibitory activity on aldose reductase in vitro.

EXPERIMENT 2

[Inhibitory activity on aldose reductase in vivo]

In order to estimate whether the compounds are available for inhibiting the enzyme in vivo, following preliminary test was carried out.

The compounds of this invention were administered orally to rats at a dose of 25 mg/kg. 2 and 5 hours later, blood samples were taken from the rats. A 0.5 ml of serum, instead of the compound, was added to the assay system described in Experiment 1. Inhibition % of the serum from rats which were administered with the compounds are shown in Table 2.

TABLE 2

| | Inhibition % on aldose reductase in vivo Time after adminstration | |
| --- | --- | --- |
| Compound of | 2 hr | 5 hr |
| Example 1 | 61.2 | 49.8 |
| Example 2 | 71.7 | 68.5 |
| Example 3 | 53.3 | 42.6 |
| Example 4 | 71.5 | 70.2 |
| Example 5 | 52.3 | 47.6 |
| Example 6 | 11.8 | 13.4 |
| Example 7 | 48.4 | 33.8 |
| Example 8 | 62.5 | 61.4 |
| Example 11 | 72.3 | 71.3 |
| Example 12 | 72.3 | 73.9 |
| Example 13 | 78.2 | 81.2 |
| Example 14 | 75.1 | 75.8 |
| Example 15 | 74.9 | 75.2 |
| standard drug* | 79.8 | 79.5 |

*note; Sorbinil

The compounds of this invention have a potent inhibitory activity on aldose reductase in vivo and are useful for treatment of diabetes mellitus with complications.

EXPERIMENT 3

[Anti-convulsion test]

The compounds of this invention may be characterized by the absence of anti-convulsion activity.

Mice (ICR stain) were administered orally with the compound of Example 2 at various doses of 50, 200, 500 and 800 mg/kg and injected with pentylenetetrazole at a dose of 100 mg/kg intraperitoneally 2 hours later.

The compound of Example 2 did not show any suppressive effect pentylenetetrazole convulsion, but Sorbinil and anti-convulsant agent phenytoin show a dose-dependent protection against the tonic convulsion. FIG. 1 shows dose-response curves for anti-convulsion activities of these compounds.

EXPERIMENT 4

[Acute toxicity on mice]

Acute toxicity was tested by oral administration with the compounds of this invention in fasted mice (ICR stain). $LD_{50}$ values are shown in Table 3.

TABLE 3

| Compound of | $LD_{50}$ |
| --- | --- |
| Example 6 | >2 g/kg |
| Example 8 | >2 g/kg |
| Example 12 | >2 g/kg |
| Example 13 | >2 g/kg |
| Example 14 | >1 g/kg |
| Example 16 | >2 g/kg |

The low toxicity of the compounds of this invention are clarified by this result.

These data suggest that the compounds of this invention are safety and able to administer to subjects with chronic diabetic complications over long period of time without any adverse effects.

The present invention is illustrated in further detail by the following Reference examples concerning to starting materials and followed by the Examples of this invention.

The starting materials of formula [VIII] were obtained as follows.

REFERENCE EXAMPLE 1

5,6-Dihydro-4H-pyrrolo[3,2,1-ij]quinoline-1,2-dione (a)

1,2,3,4-tetrahydroquinolinecarbonylmethylpyridinium chloride

Chloroacetyl chloride (22.6 g, 0.2 mole) in dry benzene (30 ml) was added dropwise to a stirred and ice cooled solution of 1,2,3,4-tetrahydroquinoline (26.6 g, 0.2 mole) in dry benzene (200 ml) containing of pyridine (15.8 g, 0.2 mole), and then stirred at room temperature for an hour. The reaction mixture was treated with water (200 ml) to dissolve precipitated salts, extracted with benzene, washed with water and dried $Na_2SO_4$. The solvent was evaporated in vacuo to yield crude 1-chloroacetyl-1,2,3,4-tetrahydroquinoline, which was used without further purification.

The mixture of above chloroacetyl derivatives and pyridine (200 ml) was refluxed for 10 minutes and then cooled to a room temperature. The resultant precipitate was collected by filtration, washed with pyridine and dried, which was recrystallized from a mixture of ethanol and petroleum ether affording of the product (52.2 g, 90.4%) as colourless plates, mp. 211°–212° C.

Such a pyridinum salt is generally moisture-sensitive, which has to be used immediately in the next step.

(b)

1-[2-(p-Dimethylaminophenyl)iminoacetyl]-1,2,3,4-tetrahydroquinoline N'-oxide

A solution of p-nitroso-N,N-dimethylaniline (27.7 g, 0.18 mole) in DFM (180 ml) was added to the above pyridinium chloride (52.2 g, 0.18 mole) in water (180 ml). The mixture was cooled to 0° C., and 2N-sodium hydroxide (90.5 ml) was added dropwise with vigorous stirring. During the addition, a viscous tar was separated and stirring continued for a half hour at room temperature. After water (600 ml) was added dropwise with vigorous stirring allowing to form a solid, the solid was collected by filtration, washed with water and dried, yielding yellow brown powder quantitatively. The product was used without further purification, but recrystallization of small portion from ethanol afforded yellow needles, mp. 130° C. (decomp.).

(c) 5,6-Dihydro-4H-pyrrolo[3,2,1-ij]quinoline-1,2-dione

The crude product (58.0 g, 0.18 mole) from part (b) was added portionwise with stirring to 6N-hydrochloric acid (120 ml) and the mixture allowed to stand for overnight. The red precipitate was collected by filtration, washed with water and dried. Recrystallization from ethanol afford the product (8.5 g, 54.6%) as dark red prisms, mp. 199° C.

Its physical properties are identical with the compound reported by J. Martinet (Compt. rend., 166, 998, '18).

REFERENCE EXAMPLE 2

5,6-Dihydro-4-methyl-4H-pyrrolo[3,2,1-ij]quinoline-1,2-dione

The procedure described in Reference example 1 was repeated using 1,2,3,4-tetrahydroquinolidine as starting material. 5,6-Dihydro-4-methyl-4H-pyrrlo[3,2,1-ij]quinoline-1,2-dione was obtained in 60.4% of overall yield, mp. 241°–243° C. (from ethanol).

REFERENCE EXAMPLE 3

5,6-Dihydro-8-methyl-4H-pyrrolo[3,2,1-ij]quinoline-1,2-dione

The procedure described in Reference example 1 was repeated using 6-methyl-1,2,3,4-tetrahydroquinoline as starting material. 5,6-Dihydro-8-methyl-4H-pyrrolo[3,2,1-ij]quinoline-1,2,-dione was obtained in 39.9% of overall yield, mp. 188°–188.5° C. (from ethanol).

REFERENCE EXAMPLE 4

2,3-Dihydropyrrolo[1,2,3-de]1,4-benzoxazine-5,6-dione (a) 3,4-Dihydro-2H-1,4-benzoxazino-4-carbonylmethyl pyridinium chloride By the procedure similar to that described in part (a) of Reference example 1., 4-chloroacetyl-3,4-dihydro-2H-1,4-benzoxazine was prepared from 3,4-dihydro-2H-1,4-benzoxazine (25.0 g, 0.185 mole) and yield was 36.9 g (94.4%), mp. 107°–108° C. as crude mass.

Above 4-chloroacetyl derivative was reacted with pyridine to afford 49.1 g (93.2%) of 3,4-dihydro-2H-1,4-benzoxazino-4-carbonylmethylpyridinium chloride, mp. 256°–257° C. (decomp.), after recrystallization from ethanol.

(b)

4-[2-(p-Dimethylaminophenyl)iminoacetyl]-3,4-dihydro-2H-1,4-benzoxazine N'-oxide By the procedure similar to that described in part (b) of Reference example 1, there was obtained 53 g of the nitrone as crude mass, which was used without further purification. Small quantity was recrystallized from ethanol to afford yellow needles melting at 147°–150° C. (decomp.).

(c)

2,3-Dihydropyrrolo[1,2,3-de][1,4]benzoxazine-5,6-dione

The above nitrone (53 g) was added portionwise with stirring to ice-cooled concentrated hydrochloric acid (100 ml). The mixture was stirred for 3 hours at room temperature and diluted with water (160 ml). The red precipitate was collected by filtration, washed with water and recrystallized from acetonitrile to yield 13.5 g (40.6% of overall yield) of red prisms, mp. 188°–188.5° C.

REFERENCE EXAMPLE 5

Pyrrolo[3,2,1-kl]phenothiazine-1,2-dione

The procedure described in Reference example 4, was repeated using phenothiazine as starting material. Pyrrolo[3,2,1-kl]phenothiazine-1,2-dione was obtained in 40% of overall yield, mp. 203°–205.5° C. (from ethanol). Its physical properties were identical with the compound reported by V. Boekalheid et al. (J. Org. Chem., 36, 2437 '71).

REFERENCE EXAMPLE 6 TO 11

By the procedure similar to that described in Reference example 4., the following novel compounds (formula [VIII]) were prepared starting from the appropriate substituted 3,4-dihydro-2H-1,4-benzoxazine or 3,4-dihydro-2H-1,4-benzothiazine.

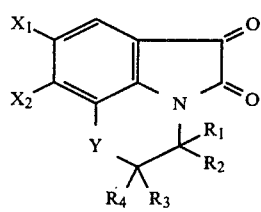

[VIII]

| Reference example | Y | $X_1$ | $X_2$ | $R_1,R_2,$ $R_3,R_4$ | mp. °C.* |
|---|---|---|---|---|---|
| 6 | S | H | H | H | 168–170 (EtOH:CH$_3$CN = 25:1) |
| 7 | O | H | Cl | H | 242–243 (CH$_3$CN) |
| 8 | O | F | H | H | 171–172 (EtOH) |
| 9 | O | F | F | H | 185–186 (EtOH) |
| 10 | O | CH$_3$ | H | H | 227–228 (CH$_3$CN) |
| 11 | O | OCH$_3$ | H | H | 167–168 (CH$_3$CN) |

*note; recrystallization solvent

REFERENCE EXAMPLE 12

8-Chloro-5,6-dihydro-4H-pyrrolo[3,2,1-ij]quinoline-1,2-dione

A mixture of 5,6-dihydro-4H-pyrrolo[3,2,1-ij]quinoline-1,2-dione (7.49 g, 0.04 mole) and N-chlorosuccinimide (5.34 g, 0.04 mole) in carbon tetrachloride (40 ml) was refluxed for 23 hours. After cooling, the resultant red precipitate was collected by filteration, washed with water and dried. Recrystallization from acetonitrile afforded 4.2 g (47.4%) of red needles, melted at 188°–189° C.

REFERENCE EXAMPLE 13

8-Chloro-5,6-dihydro-4-methyl-4H-pyrrolo[3,2,1-ij]quinoline-1,2-dione

To a suspension of 8.05 g (0.04 mole) of 5,6-dihydro-4-methyl-4H-pyrrolo[3,2,1-ij]quinoline-1,2-dione in carbon tetrachloride (50 ml) was added 5.74 g (0.043 mole) of sulfuryl chloride and the mixture was refluxed for 24 hours. After cooling, there was obtained 4.4 g of red crystals. Recrystallization from ethanol afforded 2.93 g (31.1%) of red prisms, melted at 152°–154° C.

REFERENCE EXAMPLE 14

8-Chloro-2,3-dihydropyrrolo[1,2,3-de][1,4-benzoxazine-5,6-dione

To a stirred solution of 2,3-dihydropyrrolo[1,2,3-de][1,4]benzoxazine-5,6-dione (28.4 g, 0.15 mole) in acetic acid (200 ml) was added dropwise 16.2 ml (0.2 mole) of sulfuryl chloride at room temperature. After stirring for 2 hours, the mixture was refluxed for an hour. Water (600 ml) was added to the reaction mixture and the resultant precipitate was collected by filtration, washed with water and dried to yield 28.5 g (85.1%) of the almost red microcrystals. Recrystallization of a portion from acetonitrile afforded red prisms, mp. 196°–197° C.

REFERENCE EXAMPLE 15

8,9-Dichloro-2,3-dihydropyrrolo[1,2,3-de][1,4]benzoxazine-5,6-dione

The procedure described in Reference example 14 was repeated using 9-chloro-2,3-dihydropyrrolo[1,2,3-de][1,4]benzoxazine-5,6-dione (the compound of Reference example 7) and yield was 81.5%, mp. 237°–238° C.

The starting materials of the formula [V] to prepare the compounds of this invention were obtained as follows.

REFERENCE EXAMPLE 16

Ethyl α-cyano-5,6-dihydro-2-oxo-$\Delta^{1,\alpha}$-4H-pyrrolo[3,2,1-ij]quinoline acetate A mixture of 5,6-dihydro-4H-pyrrolo[3,2,1-ij]quinoline-1,2-dione (7.49 g, 0.04 mole) and ethyl cyanoacetate (4.89 g, 0.044 mole) in ethanol (75 ml) containing of piperidine (0.2 ml) was refluxed for 3 hours. After cooling, the precipitate was collected by filtration, washed with a portion of ethanol and dried, yielding 9.1 g (80.6%) of the almost pure acetate. Recrystallization of a portion from ethanol afforded purple plates, mp., 170°–172° C.

REFERENCE EXAMPLE 17 TO 30

By the procedure similar to that described in Reference example 16, the following novel compounds of the formula [V] were prepared starting from those of the formula [VIII].

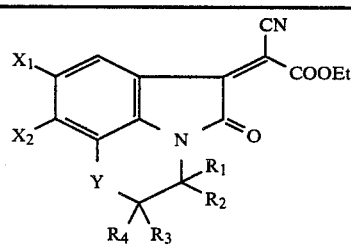

[V]

| Reference example | Y | $X_1$ | $X_2$ | $R_1$ | $R_2,$ $R_3,R_4$ | mp. °C.** |
|---|---|---|---|---|---|---|
| 17 | CH$_2$ | Cl | H | H | H | 175–177 (EtOH) |
| 18 | CH$_2$ | CH$_3$ | H | H | H | 153–155 (CH$_3$CN) |
| 19 | CH$_2$ | H | H | CH$_3$ | H | 103–105 (EtOH) |
| 20 | CH$_2$ | Cl | H | CH$_3$ | H | 187–188.5 (CH$_3$CN) |
| 21 | O | H | H | H | H | 174–176 (CH$_3$CN:EtOH = 3:1) |
| 22 | S | H | H | H | ⟨benzene ring⟩ | 195–197 (CH$_3$CN) |
| 23 | S | H | H | H | H | 150–152 (CH$_3$CN) |
| 24 | O | Cl | H | H | | 172–173 (EtOH:CH$_3$CN = 5:1) |
| 25 | O | H | Cl | | | 180–182* |
| 26 | O | Cl | Cl | | | 235–237 (CH$_3$CN) |
| 27 | O | F | H | | | 198–199* |
| 28 | O | F | F | | | 178–180* |
| 29 | O | CH$_3$ | H | | | 192–194 (CH$_3$CN) |

13

-continued

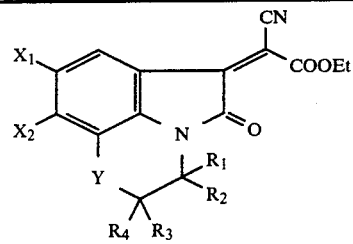

| Reference example | Y | $X_1$ | $X_2$ | $R_1$ | $R_2$, $R_3$, $R_4$ | mp. °C.** |
|---|---|---|---|---|---|---|
| 30 | O | | $OCH_3$ | H | | 196–198* |

*note; essentially pure by TLC ($SiO_2$, $C_6H_6$:$CH_3CN$ = 3:1)
**note; recrystallization solvent Now the compounds of this invention of the formula [I] were obtained as follows. It will be understood, however, that the invention is not limited to the specific details of these examples.

EXAMPLE 1

5′,6′-Dihydrospiro[pyrrolidine-3,1′-[4H]pyrrolo[3,2,1-ij]quinoline]-2,2′,5(1′H)-trione To a suspension of ethyl α-cyano-5,6-dihydro-2-oxo-$\Delta^{1,\alpha}$-4H-pyrrolo[3,2,1-ij]quinolineacetate (8.47 g, 0.03 mole) in methanol (30 ml) was added potassium cyanide (2.93 g, 0.04 mole) and the mixture was stirred for 3 hours room temperature. The resultant solution was cooled to 0° C., saturated with hydrogen chloride gas and allowed to stand overnight. The mixture was warmed at 50° C. for an hour and refluxed for 4 hours. After cooling, an addition of water (30 ml) gave a viscous tar containing 4-methoxycarbonyl-5′,6′-dihydrospiro[pyrrolidine-3,1′-[4H]pyrrolo[3,2,1-ij]quinoline]-2,2′,5(1′H)-trione, which was extracted with benzene, washed with water and dried. Evaporation of the benzene afforded yellow oily residue, to which was added 40 ml of acetic acid and refluxed for 10 hours. After evaporation of the solvent, the residue was treated with benzene to give a fine solid. Recrystallization from ethanol yielded 2.92 g (38.0%) of 5′,6′-dihydrospiro[-pyrrolidine-3,1′-[4H]pyrrolo[3,2,1-ij]quinoline]-2,2′,5(1′H)-trione, as colorless needles, mp. 253°–255° C.

Analysis: Calcd. for $C_{14}H_{12}N_2O_3$: C, 70.58; H, 4.85; N, 7.48%. Found: C, 70.52; H, 4.67; N, 7.40%.

EXAMPLE 2

8′-Chloro-5′,6′-dihydrospiro[pyrrolidine-3,1′-[4H]pyrrolo[3,2,1-ij]quinoline]-2,2′,5(1′H)-trione The procedure described in Example 1 was repeated using the product of Reference example 16 as starting material. There was obtained in 38.5% yield as colorless microcrystals, mp. 268°–269° C. (from methanol)

Analysis: Calcd. for $C_{14}H_{11}ClN_2O_3$: C, 57.84; H, 3.81; N, 9.64%. Found: C, 57.93; H, 3.70; N, 9.68%

This compound was also prepared from the compound of Example 1 by the method described in Example 8.

EXAMPLE 3 TO 5

Using a similar procedure described in Example 1, the following compounds of the formula [I] were obtained in yield of 28 to 52% starting from appropriate compounds of the formula [V].

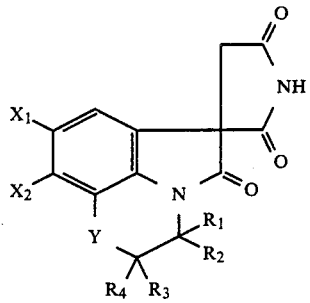

| Example | Y | $X_1$ | $X_2$ | $R_1$ | $R_2$ $R_3$ $R_4$ | mp °C.* | Analysis (%) Calcd. (upper) Found (Lower) | | |
|---|---|---|---|---|---|---|---|---|---|
| | | | | | | | C | H | N |
| 3 | $CH_2$ | H | H | $CH_3$ | H | 209–211 (EtOH) | 66.65 66.73 | 5.22 5.12 | 10.37 10.37 |
| 4 | $CH_2$ | Cl | H | $CH_3$ | | 263–266 ($CH_3CN$) | 59.12 59.07 | 4.30 4.14 | 9.20 9.23 |
| 5 | O | H | H | H | | 211–212 (ACOH) | 60.46 60.29 | 3.90 3.70 | 10.85 10.82 |

*note; recrystallization solvent

EXAMPLE 6

Spiro[pyrrolidine-3,2′-pyrrolo[3,2,1-kl]phenothiazine]-1′,2,5(2′H)-trione (a)

4-methoxycarbonylspiro[pyrrolidine-3,2′-pyrrolo[3,2,1-kl]phenothiazine]-1′,2,5(2′H)-trione A mixture of ethyl α-cyano-1-oxo-$\Delta^{2,\alpha}$-pyrrolo[3,2,1-kl]phenothiazineacetate (the compound of Reference example 22, 6.79 g, 0.02 mole), methanol (25 ml) and potassium cyanide (1.82 g, 0.28 mole) was stirred for 2 hours at 30° to 40° C.

The solution was saturated with hydrogen chloride gas under cooling and then allowed to stand for overnight. Finally, the reactant was warmed at 50° C. for an hour, refluxed for 4 hours and poured into water to give a colorless powder. The powder was collected by filtration, washed successively with water and benzene, and then dried. Recrystallization from acetonitrile yielded 2.3 g (30.3%) of the product, mp. 221°–224° C.

(b)

Spiro[pyrrolidine-3,2′-pyrrolo[3,2,1-kl]phenothiazine]-1′,2,5(2′H)-trione

The above product from part (a) (2.2 g, 0.0058 mole) was refluxed in acetic acid (20 ml) for 9 hours. After cooling, the resultant precipitate was collected by filtration and recrystallized from acetic acid-DMSO to afford 1.38 g (73.8%) of spiro[pyrrolidine-3,2′-pyrrolo[3,2,1-kl]phenothiazine]-1′,2,5-(2′H)-trione, mp. above 300° C.

Analysis: Calcd. for $C_{17}H_{10}N_2O_3S$: C, 63.34; H, 3.13; N, 8.69%. Found: C, 73.18; H 2.93; N, 8.59%.

EXAMPLE 7

5′,6′-Dihydro-8′-methylspiro[pyrrolidine-3,1′-[4H]pyrrolo[3,2,1-ij]quinoline]-2,2′,5(1′H)-trione Using the procedure described in Example 6(a), 5′,6′-dihydro-4-methoxycarbonyl-8′-methylspiro[pyrrolidine-3,1′-[4H]pyrrolo[3,2,1-ij]quinoline]-2,2′,5(1H′)- trione was prepared in 60.9%, mp 165°–167° C., but after addition of water, the separated viscous tar was extracted with dichloromethane and recrystallized from benzene. This 4-methoxycarbonyl derivative was decarboxylated using the procedure in Example 6(b) to afford, 5',6'-dihydro-8'-methylspiro[pyrrolidine-3,1-[4H]pyrrolo[3,2,1-ij]quinoline]-2,2'5(1'H)-trione, as colorless prisms, mp. 221°–222° C. (recrystallization from ethanol).

Analysis: Calcd. for $C_{15}H_{14}N_2O_3$: C, 66.65; H, 5.22; N, 10.37%. Found: C, 66.57; H, 5.14; N, 10.32%.

EXAMPLE 8

8'-Chloro-2',3'-dihydrospiro[pyrrolidine-3,6'-pyrrolo[1,2,3-de][1,4]benzoxazine]-2,5,5'(6'H9-trione To a suspension of 2',3'-dihydrospiro[pyrrolidine-3,6'-pyrrolo[1,2,3-de][1,4]benzoxazine]-2,5,5'-(6'H)-trione (1 g, 0.0039 mole) in acetic acid (10 ml) was added sulfuryl chloride (1.05 g, 0.078 mole) and the mixture was stirred for 4 hours at room temperature. After water was added, a precipitate was collected by filtration, washed with water and dried. Recrystallization from acetic acid afforded 0.53 g (46.5%) of 8'-chloro-2',3'-dihydrospiro[pyrrolidine-3,6'-pyrrolo[1,2,3-de-9 [1,4]benzoxazine]-2,5,5'(6'H)-trione, as colorless microcrystals, mp. 260°–262° C.

Analysis: Calcd. for $C_{13}H_9ClN_2O_4$: C, 53.34; H, 3.10; N, 9.57%. Found C, 53.31; H, 2.99; N, 9.67%.

EXAMPLE 8

Sodium salt of 5',6'-dihydrospiro[pyrrolidine-3,1'-[4H]pyrrolo[3,2,1-ij]quinoline]-2,2',5(1'H)-trione 5',6'-Dihydrospiro[pyrrolidine-3,1'-[4H]pyrrolo[3,2,1-ij]quinoline]-2,2',5(1'H)-trione was dissolved in water containing equimolar sodium hydroxide and the solution was treated by freeze-drying method to give the sodium salt as an amorphous solid having a satisfactory microanalytical value.

Using the similar method, a compound of formula [I] is reacted with a cation such as alkali metals or alkaline earth metals to form a cation salt.

EXAMPLE 10

8'-Chloro-2'3'-dihydrospiro[pyrrolidine-3,6'-pyrrolo[1,2,3-de][1,4]benzoxazine]-2,5,5'(6'H)-trione Potassium cyanide (9.31 g, 0.143 mole) was added to a suspension of ethyl 8-chloro-α-cyano-2,3-dihydro-5-oxo-$\Delta^{6,\alpha}$-pyrrolo[1,2,3-de][1,4]benzoxazineacetate (the compound of Reference example 24, 30.4 g, 0.095 mole) in methanol (100 ml) and the mixture was stirred at 30° to 40° C. for 2 hours and filtered off. The filtrate was saturated with hydrogen chloride gas under cooling and allowed to stand for overnight. The mixture was warmed at 50° C. for an hour, refluxed for 4 hours and then water (100 ml) was added. The mixture was extracted with ethyl acetate, washed with water and dried. Evaporation of the solvent afforded dark yellow residue, which was refluxed with 100 ml of acetic acid for 18 hours. After evaporation of acetic acid, the residue was treated with benzene to give a solid, which was collected by filtration to afford 17.2 g (61.9 g) of the crude product. Rectystallization from acetic acid yielded 14.1 g (50.7%) of 8'-chloro-2',3'-dihydrospiro[pyrrolidine-3,6'-pyrrolo[1,2,3-de][1,4]benzoxazine]-2,5,5'-(6'H)-trione as colorless prisms, mp. 260°–262° C.

Analysis: Calcd. for $C_{13}H_9ClN_2O_4$: C, 53.34; H, 3.10; N, 9.57%. Found: C, 53.34; H, 2.98; N, 9.48%.

This compound was identical with that of Example 8 by comparison of UV, IR, NMR and mass spectra.

EXAMPLE 11 TO 17

By the procedure described in Example 10, the following novel compounds of the formula I were prepared starting from appropriate compounds of the formula [V].

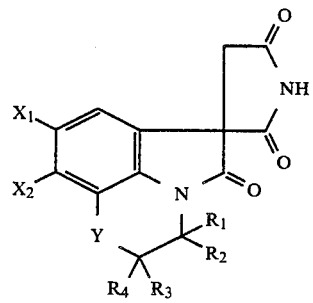

[I]

| Example | Y | $X_1$ | $X_2$ | $R_1, R_2, R_3, R_4$ | mp °C.* | Analysis (%) Calcd. (upper) Found (lower) | | |
|---|---|---|---|---|---|---|---|---|
| | | | | | | C | H | N |
| 11 | S | H | H | H | 189–190 | 56.92 | 3.67 | 10.22 |
| | | | | | (EtOH) | 57.11 | 3.56 | 10.09 |
| 12 | O | H | Cl | | 195–196 | 53.34 | 3.10 | 9.57 |
| | | | | | (EtOH) | 52.84 | 2.89 | 9.28 |
| 13 | O | Cl | Cl | | 212–212.5 | 47.73 | 2.47 | 8.57 |
| | | | | | (EtOH) | 47.48 | 2.29 | 8.51 |
| 14 | O | F | H | | 198–199 | 56.52 | 3.28 | 10.14 |
| | | | | | (isoPrOH) | 56.44 | 3.09 | 10.06 |
| 15 | O | F | F | | 208–210 | 53.07 | 2.74 | 9.52 |
| | | | | | (EtOH) | 53.04 | 2.66 | 9.52 |
| 16 | O | $CH_3$ | H | | 232 | 61.76 | 4.44 | 10.29 |
| | | | | | (EtOH) | 61.62 | 4.42 | 10.25 |
| 17 | O | $OCH_3$ | H | | 247–248 | 58.33 | 4.20 | 9.22 |
| | | | | | (EtOH) | 58.13 | 4.18 | 9.49 |

*note; Recrystallization solvent

The other preferable compounds of this invention are as follows;

8'-chloro-9'-fluoro-2',3'-dihydrospiro[pyrrolidine-3,6'-pyrrolo[1,2,3-de][1,4]benzoxazine]-2,5,5'(6'H)-trione, 9'-Chloro-8'-fluoro-2',3'-dihydrospiro[pyrrolidine-3,6'-pyrrolo[1,2,3,4-de][1,4-9 benzoxazine]-2,5,5'(6'H)-trione, 8'-Bromo-2',3'-dihydrospiro[pyrrolidine-3,6'-pyrrolo[1,2,3-de][1,4]benzoxazine-2,5,5'(6'H)-trione, 8-Chloro-2',3'-dihydrospiro[pyrrolidine-3,6'-pyrrolo[1,2,3-de][1,4]benzothiazine]-2,5,5'(6'H)-trione, 8'-Fluoro-2',3'-dihydrospiro[pyrrolidine-3,6'-pyrrolo[1,2,3-de][1',4]benzothiazine-2,5,5'(6'H)-trione.

What is claimed is:

1. Spiro-linked pyrrolidine-2,5-diones of the formula;

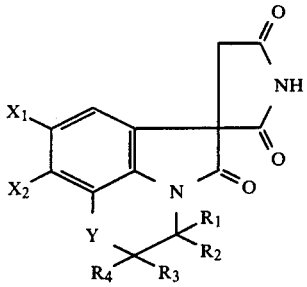

and the base salts thereof with pharmaceutically acceptable cations, wherein $X_1$ and $X_2$ each independently represent a hydrogen, a halogen atom, a lower alkyl or lower alkoxy group; Y is a methylene group, a oxygen or sulfur atom; $R_1$, $R_2$, $R_3$ and $R_4$ each independently represent a hydrogen atom, a lower alkyl group or forming a benzene ring together with their adjacent carbon atoms.

2. Compounds according to claim 1, and the salts thereof, wherein $X_1$ and $X_2$ are each a hydrogen, fluorine, chlorine, bromine atom, a methyl or methoxy group; Y is a methylene group, a oxygen or sulfur atom; $R_1$, $R_2$, $R_3$ and $R_4$ are independently a hydrogen atom, a methyl group or forming a benzene ring together with their adjacent carbon atoms.

3. Spiro-linked pyrrolidine-2,5-diones as claimed in claim 1 of the formula;

![Formula II]

and the salts thereof, wherein $X_1$ and $X_2$ each independently represent a hydrogen, a halogen atom, a lower alkyl or lower alkoxy group; $R_1$, $R_2$, $R_3$ and $R_4$ each independently represent a hydrogen atom, a lower alkyl group and forming a benzene ring together with their adjacent carbon atoms.

4. Compounds as claimed in claim 3 and the salts thereof, $X_1$ and $X_2$ are each a hydrogen, fluorine, chlorine, bromine atom, a methyl or methoxy group and $R_1$, $R_2$, $R_3$ and $R_4$ are independently a hydrogen atom, a methyl group or forming a benzene ring together with their adjacent carbon atoms.

5. Spiro-linked pyrrolidine-2,5-diones as claimed in claim 1 of the formula;

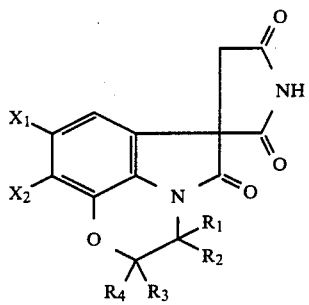

and the salts thereof, wherein $X_1$, $X_2$, $R_1$, $R_2$, $R_3$ and $R_4$ mean as defined terms in claim 1.

6. Compounds as claimed in claim 5 and the salts thereof, wherein $X_1$ and $X_2$ are each a hydrogen, fluorine, bromine atom, a methyl or methoxy group and $R_1$, $R_2$, $R_3$ and $R_4$ are independently a hydrogen atom, methyl group or forming a benzene ring together with their adjacent carbon atoms.

7. Spiro-linked pyrrolidine-2,5-diones as claimed in claim 1 of the formula;

![Formula IV]

and the salts thereof, wherein $X_1$, $X_2$, $R_1$, $R_2$, $R_3$ and $R_4$ mean as defined terms in claim 1.

8. Compounds as claimed in claim 7 and the salts thereof, wherein $X_1$ and $X_2$ are each a hydrogen, fluorine, chlorine, bromine atom, a methyl or methoxy group and $R_1$, $R_2$, $R_3$ and $R_4$ are independently a hydrogen atom, a methyl group or forming a benzene ring together with their adjacent carbon atoms.

* * * * *

UNITED STATES PATENT AND TRADEMARK OFFICE
CERTIFICATE OF CORRECTION

PATENT NO. : 4,593,092

DATED : JUNE 3, 1986

INVENTOR(S) : TSUTOMU IRIKURA ET AL

It is certified that error appears in the above-identified patent and that said Letters Patent is hereby corrected as shown below:

Column 1, line 38;

"olyols." should read "polyols.",

Column 4, line 18;

"[I" should read "[I]",

Column 6, line 27;

"-2h-" should read "-2H-",

Column 11, line 57;

"[1,4-" should read "[1,4]",

Column 13, line 33;

"room" should read "at room",

Column 15, line 26;

"[1,2,3-de-9" should read "[1,2,3-de]",

Column 15, line 30;

"EXAMPLE 8" should read "EXAMPLE 9",

UNITED STATES PATENT AND TRADEMARK OFFICE
CERTIFICATE OF CORRECTION

PATENT NO. : 4,593,092

DATED : JUNE 3, 1986

INVENTOR(S) : TSUTOMU IRIKURA ET AL

It is certified that error appears in the above-identified patent and that said Letters Patent is hereby corrected as shown below:

Column 16, line 10;

"formula I" should read "formula [I]",

Column 16, line 56;

"[1,4-9" should read "[1,4]".

Signed and Sealed this

Thirtieth Day of September 1986

[SEAL]

Attest:

DONALD J. QUIGG

Attesting Officer

Commissioner of Patents and Trademarks